United States Patent [19]
Schneider et al.

[11] 4,158,560
[45] Jun. 19, 1979

[54] BROAD SPECTRUM HERBICIDAL DIACYLIMIDE COMPOSITIONS

[75] Inventors: Louis Schneider, Elizabeth; David E. Graham, Westfield, both of N.J.

[73] Assignee: GAF Corporation, New York, N.Y.

[21] Appl. No.: 852,460

[22] Filed: Nov. 17, 1977

[51] Int. Cl.² .................................................. A01N 9/20
[52] U.S. Cl. ............................................ 71/118; 71/66
[58] Field of Search ............................................ 71/118

[56] References Cited

U.S. PATENT DOCUMENTS

| | | | |
|---|---|---|---|
| 3,158,650 | 11/1964 | Weil et al. | 71/118 X |
| 3,959,370 | 5/1976 | Watts, Jr. | 71/118 X |

FOREIGN PATENT DOCUMENTS 421313  1/1967  Japan .......................................... 71/118

OTHER PUBLICATIONS

Durrell et al., The reaction of Nitriles with Carboxylic Acids., J. Organic Chem., pp. 831–833, (1963).

Primary Examiner—Catherine L. Mills
Attorney, Agent, or Firm—Walter C. Kehm; Walter Katz

[57] ABSTRACT

The invention provides broad spectrum herbicidal diacylimide compositions which include compounds having the formula:

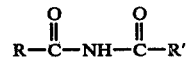

where R and R' are selected from alkyl, alkenyl, haloalkyl and haloalkenyl having from 1–5 carbon atoms, being the same or different groups. The compositions of this invention show excellent agricultural herbicidal activity, particularly against foxtail millet, Japanese millet, crabgrass and pigweed, and aquatic herbicidal activity against lower and higher submerged aquatic plants.

2 Claims, No Drawings

BROAD SPECTRUM HERBICIDAL DIACYLIMIDE COMPOSITIONS

BACKGROUND OF THE DISCLOSURE

1. Field of the Invention

This invention relates to novel herbicidal diacylimide compositions which exhibit excellent agricultural and aquatic herbicidal activity.

2. Description of the Prior Art

Many compositions are known in the literature which are active as herbicides, however, rarely are compounds which show broad spectrum herbicidal activity, particularly against many agricultural and aquatic weeds.

SUMMARY OF THE INVENTION

The invention provides broad spectrum herbicidal diacylimide compositions which include compounds having the formula:

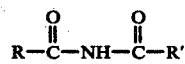

where R and R' are selected from alkyl, alkenyl, haloalkyl and haloalkenyl having from 1-5 carbon atoms, being the same or different groups.

The compositions of this invention show excellent agricultural herbicidal activity, particularly against foxtail millet, Japanese millet, crabgrass and pigweed, and aquatic herbicidal activity against lower and higher submerged aquatic plants.

DETAILED DESCRIPTION OF THE INVENTION

The herbicidal compounds of the invention are prepared from a suitable amide I which is condensed with an acyl halide II to provide the desired diacylimide compound III, as follows:

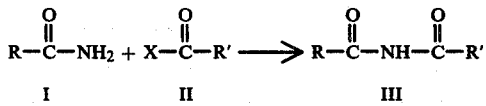

where R and R' are previously defined, and X is a halogen.

Both the acyl halide and amide starting materials usually are commercially available; however, if necessary, the acyl halide may be readily prepared from the corresponding acid by reaction with a suitable acyl halide, such as thionyl chloride. The amide may be readily prepared, for example, from the corresponding acyl halide by reaction with ammonia.

A. AGRICULTURAL HERBICIDAL ACTIVITY

As agricultural herbicides, the compositions of this invention usually are applied to the soil at the rate of about 1 to 25 lbs. per acre or as a foliar spray at concentrations of about 31 to 250 ppm. They show particularly effective herbicidal activity against such weeds as foxtail millet, Japanese millet, crabgrass and pigweed.

The materials of the present invention may be applied to the soil or sprayed on the weeds on site at a rate of about 1 or less to about 25 pounds per acre depending on various circumstances of the susceptibility of the weed to the herbicide, the weather, the stage of growth and various other factors. The material may be applied as a dust or spray. As a dust, it is more practical to extend it with diluents such as bentonite, chalk, clay, diatomaceous earth, fullers earth, mica, ground slate or any of the other usual carriers for agricultural chemicals. As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

AGRICULTURAL HERBICIDAL TESTS

Primary tests on the compositions of the invention were made on two flats seeded with six species of representative monocotyledonous and dicotyledonous plants, e.g. foxtail millet, Japanese millet and crabgrass. The test chemical was applied to one such flat immediately after it was seeded. The other flat contained plants on which the first true leaves had developed. These flats were sprayed, simultaneously, with the test chemical at 2080 ppm, a rate sufficient to give 10 lb/acre (104 mg in 50 ml of water on 144 square inches). Diuron, 3-(3,4-dichlorophenyl)-1,1- dimethylurea, as a standard, was applied post-emergence at the rate of 2.5 lb/acre. The response was rated 12 to 21 days after treatment on a scale of 0 to 10 where 0 represents no injury and 10 represents complete kill.

Table I

Agricultural Herbicidal Test Data $$R-\overset{O}{\underset{\|}{C}}-NH-\overset{O}{\underset{\|}{C}}-R'$$

Primary Screening Post-Emergence Herbical Activity (10 lbs./acre)

| Compound # B-T | GAF # | R | R' | Foxtail Millet | Japanese Millet | Crabgrass | Pigweed |
|---|---|---|---|---|---|---|---|
| 49 | 6672 | CH$_2$=CH— | —CH$_2$=CH$_2$ | 10 | 8 | 9 | 10 |
| 519 | 7282 | ClCH$_2$CH$_2$— | —CH$_2$Br | 8 | ? | 8 | 9 |
| 410 | 7202 | ClCH$_2$— | —CH$_2$CH$_3$ | 8 | 5 | 8 | 8 |
| 409 | 7201 | ClCH$_2$CH$_2$— | —CCl=CHCl | 10 | 8 | 8 | 10 |
| 406 | 7198 | CH$_3$— | —CCl=CHCl | 9 | 4 | 9 | 8 |
| 427 | 7227 | CH$_2$Br— | —CCl=CHCl | 10 | 9 | 9 | 9 |
| 153 | 6792 | CH$_3$— | —CH=CH$_2$ | 10 | 9 | 10 | 8 |
| 311 | 7129 | ClCH$_2$— | —CH=CH$_2$ | 10 | 9 | 9 | 10 |
| 398 | 7192 | CH$_3$CH$_2$CH$_2$— | —CCl=CHCl | 10 | 9 | 6 | 10 |
| 401 | 7193 | CHCl$_2$— | —CCl=CHCl | 9 | 5 | 9 | 10 |
| 763 | 7519 | ClCH$_2$CH$_2$— | —CCl=CHCl | 8 | 4 | 9 | 10 |
| 367 | 7181 | ClCH$_2$— | —CCl=CHCl | 10 | 8 | 10 | 10 |
| 368 | 7182 | CH$_2$=CH$_2$— | —CH$_2$—CH$_3$ | 10 | 9 | 10 | 10 |

Table I-continued

Agricultural Herbicidal Test Data

Primary Screening Post-Emergence Herbical Activity (10 lbs./acre)

| Compound # B-T | GAF # | R | R' | Foxtail Millet | Japanese Millet | Crabgrass | Pigweed |
|---|---|---|---|---|---|---|---|
| Control | | Diuron | | 10 | 10 | 10 | 10 |

B. AQUATIC HERBICIDAL ACTIVITY

The compounds of this invention also are useful as aquatic herbicides. Several aquatic plants were used for such tests. For example, a number of cultures of the duckweed plant, Lemna minor L., were collected from a small pond surface sterilized by a brief immersion in a 10% solution of Clorox ® bleach and tested for bacterial and algal contaminations. Contaminated cultures were discarded, and a single vigorous plant was selected for the vegetative propagation of axenic cultures. Since all subsequent cultures consist of progeny of the original plant, a genetically homogenous clone has been maintained by weekly transfer of sub-cultures to fresh media.

For phytotoxicity assays, stock culture plants were randomly selected and placed in 100 ml of modified Hoagland's solution in 250 ml Erlenmeyer flasks to which the herbicides had been added at a concentration of 100 ppm. After inoculation, each test flask contained 25 plants as did the control flasks and the flasks containing the standard herbicide, Diquat ®. The cultures in triplicate were maintained in a growth chamber at 25° C. under a light intensity of 1000 foot-candles on a photoperiod of 16 hours.

To treat or assay higher submerged aquatic plants, for example, Myriophyllum and Vallisneria, stock cultures of each species were prepared and maintained in an aquarium filled with pond water from a small pond. These aquaria were maintained at 20° C . under small aquarium lights on a 16-hour photoperiod.

For phytotoxicity tests 2-liter battery jars were filled with pond water and one plant was placed in each battery jar from each stock species. These were allowed to root for a week to 10 days under the same controlled conditions as the stock aquaria in a 2-inch layer of sand covering the bottom of the battery jar. After 10 days the test chemicals were added at 10 ppm to each battery jar. Three replicate battery jars were included for each test chemical. Similarly, plants in three untreated battery jars served as controls. Three battery jars treated with Endothall ® at 2.5 ppm served as the standard of comparison.

AQUATIC HERBICIDE TESTS

A. Lemna Minor

At the end of a two-week test period those fronds that were chlorotic over half their surface were counted 'dead'. Compounds that caused 80% mortality when applied at 100 ppm were tested in dosage series. The data presented in Table II below indicates that at a concentration of 100 ppm duckweed was completely killed by compound 7,181, in Table I (also Example 1).

Table II

| Phytotoxicity against Lemna minor. | | |
|---|---|---|
| Concentration (ppm) | Compound % Kill[A] | |
| | 7,181 | Diquat ® |
| 100 | 100 | 100 |
| 50 | 100 | — |
| 25 | 100 | — |
| 12.5 | 100 | 100 |

Note: No dead fronds were observed in the control flasks.
[a]Fronds that were chlorotic over half their surface were counted as 'dead', and the number of dead fronds was then expressed as a percentage of the total number of fronds receiving a given treatment.

B. Higher Aquatic Plants

Phytotoxicity ratings were made on the higher plants in each battery jar after a 2-week test period. Ratings were based on a 0–10 scale with 10 signifying complete mortality and 0 indicating no injury. Each chemical was replicated three times.

Against submerged aquatic macrophytes in initial tests (Table III) the compound 7,181 was effective in controlling the three aquatic macrophyte species. In dosage-series compound 7,181 also gave some control in concentrations as low as 5 ppm.

Table III

| Phytotoxicity against Higher Submerged Aquatic Macrophytes. | | | |
|---|---|---|---|
| Treatment Applied | | Phytotoxicity Rating[a] | |
| Compound | Concentration (ppm) | Myriophyllum spp. | Vallisneria spp. |
| 7,181[b] | 5 | 9.3 | 10.0 |
| Endothall ® | 2.5 | 9.0 | 6.7 |
| Control | 4.3 | 4.3 | 1.0 |

[a]Phytotoxicity rated on a scale of 0-10 where 0 = no plant injury and 10 = complete kill. Each value reported in the average of three replicates.
[b]Initial testing at 5 ppm against Vallisneria and Myriophyllum only in a separate test.

The invention will be illustrated more, particularly by the following non-limiting specific examples by which the compounds in Table I are prepared.

EXAMPLE 1

N-CHLOROACETYL-N-2,3-DICHLOROACRYLOYLIMIDE

A. 2,3-Dichloroacryloylchloride 2,3-Dichloroacrylic acid (211.5 g. 1.5 moles), thionyl chloride (357.0 g, 3.0 moles), dimethylformamide (7 cc) and benzene (300 cc) were charged into a 1-liter, 4-neck flask and heated at reflux for 8 hrs. The benzene and excess thionyl chloride were removed atmospherically and 174.5 g (73% yield) of product was distilled at 65°–67° C./23 mm.

B. 2,3-Dichloroacrylamide 2,3-Dichloroacryloylchloride (174.5 g, 1.1 moles) was added to a 3-liter beaker precharged with aqueous ammonia (266 cc. 4.4 moles) and ice (500 cc). The mixture was stirred for ½ hr. at 0°–5° C., filtered and washed with cold water yielding 135 g of amide (88%), m.p. 135°-136° C.

Anal: Calc'd for $C_3H_3Cl_2NO$: Cl, 50.71; N, 10.0. Found: Cl, 50.07; N, 9,69.

C. N-Chloroacetyl-N-2,3-Dichloroacryloylimide

Toluene (150 cc), 2,3-dichloroacrylamide (52.0 g, 0.37 mole) were charged into a 500 cc, 4-neck flask. Then chloroacetyl chloride (42.0 g, 0.37 mole) was added and the reaction mixture was heated at reflux for 22 hrs. The mixture was cooled to 25° C. and the product filtered, washed with cold toluene and vacuum dried yielding 51 g (63.8%) m.p. 99°-100° C.

Anal: Calc'd for $C_5H_4Cl_3NO_2$: Cl, 49.14; N, 6.47. Found: Cl, 49.16; N, 6.20.

EXAMPLE 2

N-3-Chloropropionyl-N-2,3-Dichloroacryloylimide

Toluene (100 cc), 2,3-dichloroacrylamide (14.0 g, 0.1 mole) and 3-chloropropionyl chloride (12.6 g, 0.1 mole) were reacted and worked-up in a similar fashion as described in Example 1 to yield 13 g (56.6%) of product, m.p. 76°-77° C.

Anal: Calc'd for $C_6H_6Cl_3NO_2$:Cl, 45.35; N, 6.10. Found: Cl, 45.63; N, 6.02.

EXAMPLE 3

N-Chloroacetyl-N-Propionylimide

Toluene (100 cc), propionamide (7.3 g, 0.1 mole) and chloroacetyl chloride (11.3 g, 0.1 mole) were reacted and worked-up in a similar fashion as described in Example 1 to yield 5.5 g (37.2%) of product m.p. 169°-170° C.

Anal: Calc'd for $C_5H_8ClNO_2$:Cl, 23.7; N, 9.36. Found: Cl, 23.6; N, 9.52.

EXAMPLE 4

N-Bromoacetyl-N-3-Chloropropionylimide

Toluene (100 cc), 3-chloropropionamide (10.7 g, 0.1 mole) and bromoacetyl chloride (20.2 g, 0.1 mole) were reacted and worked-up in a similar fashion as described in Example 1 to yield 15.5 g (71.6%) of product m.p. 133°-134° C.

Anal: Calc'd for $C_4H_7BrClNO_2$ Total halogen (Br, Cl) 50.5; N, 6.13. Found: Total Halogen (Br, Cl) 50.2; N, 6.25.

EXAMPLE 5

N-Acryloyl-N-Chloroacetylimide

Methylene chloride (150 cc), chloroacetyl chloride (62.1 g, 0.55 mole) and acrylamide (35.5 g, 0.5 mole) were stirred at 25°-30° C. for 25 hours. The product was filtered, washed with cold methylene chloride and dried to yield 17.0 g (23.1%) of product, m.p. 175°-176° C.

Anal: Calc'd for $C_5H_6ClNO_2$:Cl, 24.0; N, 9.49. Found: Cl, 24.8; N, 9.26.

EXAMPLE 6

N-Bromoacetyl-N-2,3-Dichloroacryloylimide

Toluene (100 cc), 2,3-dichloroacrylamide (14.0 g, 0.1 mole), and bromoacetyl chloride (20.2 g, 0.1 mole) were reacted and worked-up in a similar fashion as described in Example 1 to yield 15.5 g (59.4%) of product, m.p. 121°-122° C.

Anal: Calc'd for $C_5H_4BrCl_2NO_2$ Total Halogen (Br, Cl) 57.9; N, 6.14. Found: Total Halogen (Br, Cl), 58.8; N, 5.78.

In those diacylimides listed in Table I which contain an unsubstituted alkenyl group, such as 6672, 6792, 7129 and 7182, it is preferable to obtain these compounds by dehydrohalogenation of the corresponding haloalkenyl group, as for example, by refluxing with triethyl amine. A typical preparation according to this procedure is described in the following example.

EXAMPLE 7

Bis-(acryloyl) imide

A. Bis-(3,3'-dichloropropionyl) imide

3-Chloropropionyl chloride (256.0 g, 2.0 mole) was charged to a 1 liter, 4-neck flask equipped with a stirrer, thermometer and reflux condenser and heated to 80°-85° C. Acrylamide (115.0 g, 1.6 mole) and hydroquinone (0.8 g) was added and the reaction manufactured at 90°-100° C. for ½ hour. The reaction mixture was cooled to 75° C. and poured with good stirring into 350 cc cold chloroform. The product was filtered cold and air dried yield 87.0 g (43.9%), mp 146°-147° C.

Anal: Calc'd for $C_6H_9Cl_2O_2N$:Cl, 35.9; N, 7.0. Found: Cl, 35.6; N, 6.9.

B. Bis-(acryloyl) imide

Acetone (300 cc) and Bis(3,3'-dichloropropionyl) imide (25.0 g, 0.13 mole) were added to a 1 liter 3-neck flask equipped with a stirrer, dropping funnel, reflux condenser and thermometer. Tiethylamine (30.0 g, 0.30 mole) in acetone (75 cc) was added over 45 minutes and the reaction mixture stirred at 25°-30° C. overnight. The triethylamine hydrochloride was filtered and the acetone concentrated by rotory evaporation with the temperature being maintained below 40° C. The product was filtered, washed with acidified (pH2) deionized water, and dried under vacuum yielding 7.5 g (41.4%) of product, m.p. 178°-179° C.

Anal: Calc'd for $C_6H_7O_2N$: N, 11.2. Found: N, 10.9.

What is claimed is:

1. A method of controlling agricultural weeds which comprises applying thereto a herbicidally effective amount of a diacylimide compound having the formula:

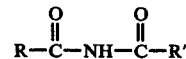

where R is a 1,2-dihaloalkenyl group having 2 carbon atoms, and R' is selected from the group consisting of alkyl and monohaloalkyl groups having from 1-3 atoms.

2. A method according to claim 1 in which said dihaloalkenyl group is —CCl=CHCl.

* * * * *